United States Patent [19]

Ross et al.

[11] Patent Number: 5,605,682
[45] Date of Patent: Feb. 25, 1997

[54] ANTIPERSPIRANT AEROSOL COMPOSITION WITH HIGH SOLIDS CONTENT

[75] Inventors: Lloyd Ross, Hampton; Frank Schebece, Edison, both of N.J.

[73] Assignee: Colgate-Palmolive Company, New York, N.Y.

[21] Appl. No.: 238,195

[22] Filed: May 4, 1994

Related U.S. Application Data

[63] Continuation of Ser. No. 869,996, Apr. 16, 1992, abandoned.

[51] Int. Cl.$^6$ .............. A61K 7/32; A61K 7/36; A61K 7/38
[52] U.S. Cl. ................ 424/68; 424/47; 424/67
[58] Field of Search ................ 424/67, 47, 68

[56] References Cited

U.S. PATENT DOCUMENTS

| | | | |
|---|---|---|---|
| 2,613,206 | 10/1952 | Caldwell | 260/233.5 |
| 3,088,874 | 5/1963 | Geary et al. | 424/67 |
| 3,198,708 | 8/1965 | Henkin et al. | 424/68 |
| 3,288,681 | 11/1966 | Goldberg | 167/90 |
| 3,395,214 | 7/1968 | Mummert | 424/47 |
| 3,725,540 | 4/1973 | Wahl | 424/67 |
| 3,773,683 | 11/1973 | Aubert | 252/305 |
| 3,790,664 | 2/1974 | Krochock et al. | 424/47 |
| 3,792,068 | 2/1974 | Luedders et al. | 260/429.3 |
| 3,929,986 | 12/1975 | Bouillon et al. | 424/46 |
| 4,045,548 | 8/1977 | Luedders et al. | 424/47 |
| 4,053,581 | 10/1977 | Pader et al. | 424/68 |
| 4,065,564 | 12/1977 | Miles, Jr. et al. | 424/66 |
| 4,073,880 | 2/1978 | Pader et al. | 424/66 |
| 4,078,051 | 3/1978 | Pomot et al. | 424/35 |
| 4,080,438 | 3/1978 | Pomot et al. | 424/35 |
| 4,080,439 | 3/1978 | Pomot et al. | 424/35 |
| 4,110,428 | 8/1978 | Kuhn et al. | 424/46 |
| 4,152,416 | 5/1979 | Sutzer et al. | 424/67 |
| 4,174,386 | 11/1979 | Spitzer et al. | 424/47 |
| 4,278,655 | 7/1981 | Elmi | 424/47 |
| 4,423,041 | 12/1983 | Clum et al. | 424/184 |
| 4,431,120 | 2/1984 | Burger | 222/192 |
| 4,806,338 | 2/1989 | Smith | 424/47 |
| 4,822,596 | 4/1989 | Callingham et al. | 424/46 |
| 4,840,786 | 6/1989 | Johnson et al. | 424/43 |
| 4,889,711 | 12/1989 | Kai et al. | 424/47 |
| 4,904,463 | 2/1990 | Johnson et al. | 424/44 |
| 4,935,224 | 6/1990 | Russo et al. | 424/47 |
| 5,017,361 | 5/1991 | Powell, Jr. et al. | 424/46 |

FOREIGN PATENT DOCUMENTS

| | | | |
|---|---|---|---|
| 75-81895 | 6/1975 | Australia | 424/68 |
| 699773 | 12/1967 | Belgium | 424/68 |
| 1076030 | 4/1980 | Canada | 424/68 |
| 0274252 | 7/1988 | European Pat. Off. | 424/68 |
| 0452762 | 10/1991 | European Pat. Off. | 424/68 |
| 2320729 | 3/1977 | France | 424/68 |
| 2274277 | 2/1984 | France | 424/68 |
| 2113706 | 8/1983 | United Kingdom | 424/68 |

OTHER PUBLICATIONS

Cosmetics and Toiletries, vol. 91, No. 1, Jan. (1976), pp. 29–32.
American Perfumer and Cosmetics, vol. 86, Oct. (1971), pp. 112–115.

*Primary Examiner*—Alan L. Rotman
*Attorney, Agent, or Firm*—Richard J. Ancel; James M. Serafino

[57] ABSTRACT

An antiperspirant aerosol composition has a level of volatile organic compounds no greater than 60 wt. %. The composition includes particulate antiperspirant material and optionally particulate filler material. The filler material may be chemically modified corn starch, micronized polyethylene, cross-linked polyurethanes, polyacrylates, talc, sodium bicarbonate, corn starch, or any combination thereof. The antiperspirant aerosol compositions includes 10–35 wt. % of particulate material, 0.2–2 wt. % of a suspending agent, 5–50 wt. % of emollient carrier liquids and no more than 60 wt. % of an aerosol propellant mixture. The particulate material consists of 25 to 100 wt. % of a particulate antiperspirant active material and 0 to 75 wt. % of a particulate filler material. In addition, the antiperspirant aerosol compositions may contain certain optional components, such as activators, germicides, medicants, perfumes and colorants.

7 Claims, No Drawings

ANTIPERSPIRANT AEROSOL COMPOSITION WITH HIGH SOLIDS CONTENT

This is a continuation of application Ser. No. 07/869,996 filed Apr. 16, 1992, now abandoned.

FIELD OF THE INVENTION

This invention relates generally to an antiperspirant aerosol composition delivered to the skin of a person through use of an aerosol delivery system. In particular, the invention relates to an antiperspirant composition of the powder suspension type suitable for spraying from a pressurized aerosol container.

BACKGROUND OF THE INVENTION

Antiperspirant compositions normally contain an astringent, such as aluminum chlorhydrate, which chemically suppresses the production of perspiration by sweat glands. This astringent is commonly applied on the skin in the form of an aerosol spray.

The antiperspirant active compound is suspended as a dry, impalpable powder in a liquid vehicle together with a non-aqueous liquified volatile propellant in a pressurized aerosol container. The aerosol spray is produced by rapid boiling of the propellant as it dispenses from the atomizing valve of the aerosol container.

The aerosol method of application has gained wide acceptance for a number of reasons. Aerosol application of an antiperspirant salt in the form of a powder suspended in the propellant is cosmetically desirable because the antiperspirant can be smoothly and effectively applied to the skin in a manner that feels dry and comfortable. Furthermore, because the antiperspirant powder does not dissolve in the liquified propellant medium, the antiperspirant salt does not corrode ordinary metal aerosol cans.

One difficulty associated with antiperspirant aerosol sprays is that the delivery of small particles of antiperspirant active compound in a finely divided spray can readily clog small valve orifices. When a residue of the liquid propellant/aerosol composition mixture remains in the valve passages following a squirt, evaporation of the liquid may lead to deposition of solid material and consequent valve clogging.

Another problem associated with conventional antiperspirant aerosol sprays is that they utilize a large amount of propellant gas. However, an aerosol composition having a high proportion of propellant is undesirable. Fluorocarbon propellants are believed to accumulate in the stratosphere, where they interfere with the protective ozone layer. In addition to contributing to air pollution, hydrocarbon propellants are flammable, requiring that the proportion of hydrocarbons be restricted to avoid a fire hazard.

Conventional antiperspirant aerosol sprays typically contain the following components: particles of an antiperspirant active compound; a suspending agent to prevent the particles of antiperspirant active compound from settling out; an emollient carrier liquid for carrying the antiperspirant particles from the container to the skin in the form of a moist spray rather than a dusty cloud to improve adherence of the antiperspirant particles to the skin; and a propellant for expelling these components from the container. Other minor additives, such as fragrance or medicant are optional.

For example, U.S. Pat. No. 3,288,681 to Goldberg et al. discloses an antiperspirant powder aerosol composition comprising an aluminum compound, e.g., aluminum chlorhydrate, alcohol, propellant and an emollient carrier, e.g., isopropyl myristate or palmitate.

U.S. Pat. No. 3,395,214 to Mummert discloses a relatively dry, collapsible foam in which an active antiperspirant material is suspended. The antiperspirant material, e.g., aluminum salt, is dispersed in a nonvolatile carrier, e.g., isopropyl myristate, with a volatile solvent, e.g., alcohol, and water to form a base. This base is then combined with a sufficient amount (10–15 wt. %) of liquified propellant. Allantoin is added to minimize irritation to skin sensitive to an aluminum based product.

U.S. Pat. No. 3,773,683 to Aubert discloses a process for preparing a propellant containing a bulking or suspending agent selected from the group of montmorillonite clays, e.g., Bentone-38. A polar liquid, e.g., propylene carbonate, is used to aid in obtaining maximum dispersion efficacy.

U.S. Pat. No. 3,792,068 to Luedders et al. discloses a powder antiperspirant active complex comprising astringent aluminum salt and zirconium salt for incorporation into powder aerosol antiperspirant compositions. One suitable suspending agent is Bentone-38. The carrier liquid may be, e.g., isopropyl palmitate, di-n-butyl phthalate, or silicone oils such as dimethylpolysiloxane.

U.S. Pat. No. 4,045,548 to Luedders et al. discloses a powder aerosol antiperspirant compositions wherein the preferred antiperspirant compound is aluminum chlorhydroxide and the preferred emollient-carrier agent is di-isopropyl adipate.

U.S. Pat. Nos. 4,053,581 and 4,073,880 to Pader et al. and 4,065,564 to Miles, Jr. et al. disclose an antiperspirant solution containing nonvolatile siloxane liquid, volatile polydimethyl siloxane liquid or both added to an alcohol solution of an aluminum chlorhydroxide complex. The siloxane reduces the tackiness of the aluminum chlorhydroxide complex during drying while substantially reducing clogging of the pump spray valve.

U.S. Pat. No. 4,110,428 to Kuhn et al. discloses an aerosol antiperspirant composition in which an antiperspirant agent, e.g., aluminum chlorhydrate, is suspended in a propellant medium containing a polyalkylene glycol to reduce staining of clothing which is accidentally exposed to the antiperspirant.

U.S. Pat. Nos. 4,078,051, 4,080,438 and 4,080,439 to Pomot et al. disclose an antiperspirant agent comprising microcrystals of an aluminum compound coated with degraded starch to provide an atomizable gel. Representative starches are waxy or ordinary corn starches degraded by acid hydrolysis.

U.S. Pat. No. 4,174,386 to Spitzer et al. discloses an aerosol antiperspirant composition comprising an astringent salt, a liquified propellant, a nonvolatile miscible organic liquid, a bulking agent and a solid aliphatic carboxylic acid to enhance adherence of the antiperspirant salt to the skin.

U.S. Pat. No. 4,278,655 to Elmi discloses an aerosol antiperspirant composition comprising an active antiperspirant salt, a hydrophobic suspending agent, a liquid carrier and a liquified propellant. In place of conventional liquid carriers such as volatile silicone, isopropyl palmitate and isopropyl myristate, benzoic acid esters are used.

U.S. Pat. No. 4,806,338 to Smith discloses an antiperspirant aerosol composition comprising 1–40% of a particulate antiperspirant material, 0.005–6.0% of a functionalized siloxane and 60–95% of an aerosol propellant. The compositions also contain a silicone gum material and a volatile silicone oil, i.e., cyclomethicone.

U.S. Pat. Nos. 4,840,786 and 4,904,463 to Johnson et al. disclose an antiperspirant aerosol composition comprising 2–10% of a hydrophobic liquid, 20–95% of a propellant, 2–30% of an enhanced efficacy metallic antiperspirant material, 0.1–3.0% of a hydrophobically treated clay suspension agent and 0.01–0.2% of an activator, such as propylene carbonate, that enables the hydrophobically treated clays to suspend the antiperspirant active compound in the hydrophobic liquid carrier.

U.S. Pat. No. 4,889,711 to Kai et al. discloses an antiperspirant aerosol composition comprising a mixed powder phase, a mixed oil phase and in excess of 90 wt. % propellant. The mixed oil phase comprises, for example, isopropyl myristate, cyclic dimethyl siloxane, bactericide and perfume. The mixed powder phase comprises aluminum hydroxychloride and a silicone-treated clay mineral. This patent also discloses comparative compositions having aluminum hydroxychloride and talc which has not been treated with silicone.

U.S. Pat. No. 4,935,224 to Russo et al. discloses an antiperspirant aerosol composition comprising an active antiperspirant salt, a silicone polymer (e.g., a silicone gum), a volatile low-viscosity fluid in which the silicone polymer is soluble (i.e., cyclomethicone) and a propellant.

Finally, U.S. Pat. No. 4,822,596 to Callingham et al. discloses an antiperspirant composition dispensed from an aerosol container which absorbs perspiration at the skin surface. The antiperspirant composition comprises a moisture-absorbent polymer in powder form, e.g., chemically modified starches. This patent also discloses that a perspiration depressant such as aluminum chlorhydrate can be incorporated along with the moisture-absorbent polymer.

The prosecution file history of the Callingham patent explicitly states that Dry Flo chemically modified corn starch does not have the moisture-absorbency properties required by the invention disclosed in that patent. In support of this thesis, Callingham et al. cited UK Patent No. 1453202, owned by Colgate-Palmolive Company, which discloses an antiperspirant composition which includes 91.54% propellant mixture, 3% aluminum chlorhydrate, 4.0% propylene glycol dipelargonate, 0.2% Bentone 38, 1.0% Dry Flo starch, 0.06% propylene carbonate, and 0.2% perfume (see Example 6). This British patent also discloses that the amount of liquid propellant can vary between 50 and 98 wt. %.

None of the patents discussed above disclose a specific formulation of an antiperspirant aerosol composition in which the amount of propellant is reduced to less than or equal to 60 wt. % by raising the particulate solids content of the composition to 10–35 wt. %. Therefore these conventional compositions are disadvantageous because greater amounts of hydrocarbons or fluorocarbons are released into the atmosphere, thereby contributing to air pollution.

SUMMARY OF THE INVENTION

One object of the present invention is to improve upon the prior art antiperspirant aerosol compositions by decreasing the amount of liquid propellants incorporated therein.

Another object of the invention is to reduce the amount of liquid propellant in an antiperspirant aerosol composition without causing clogging of the valve of the aerosol container.

It is yet another object of the invention to provide a high-solids aerosol formula with a reduced amount of propellant that has a dry feel.

Also it is an object of the invention to provide a high-solids aerosol formula with a reduced amount of propellant that is safe for human use and aesthetically acceptable.

The foregoing objects are attained by reducing the level of volatile organic compounds to a maximum of 60 wt. % and increasing the level of solids. In accordance with the preferred embodiment of the invention, filler powder(s) in addition to the active antiperspirant powder are incorporated in the formula. In particular, the filler powder may comprise talc, chemically modified corn starch, non-reactive polymers such as micronized polyethylene, polyacrylates or cross-linked polyurethanes, or any combination thereof. Although hydrophobic powders are the preferred class, powders such as sodium bicarbonate, corn starch or any vegetable-derived starches can be used provided that extraordinary care is exercised to minimize moisture contamination in the can.

The antiperspirant aerosol compositions in accordance with the preferred embodiments of the invention comprise 10 to 35 wt. % of a combination consisting of particulate antiperspirant material and particulate filler material, 0.2 to 2 wt. % of a suspending agent, 5 to 50 wt. % of emollient carrier liquid material and less than 60 wt. % of an aerosol propellant mixture. In addition, the antiperspirant aerosol compositions in accordance with the invention may contain certain optional components, such as activators, germicides, medicants, perfumes and colorants.

Alternatively, 10 to 35 wt. % of particulate antiperspirant material can be included in the formulation without any distinct particulate filler material. This is because the particulate antiperspirant material can serve the dual function of antiperspirant and filler.

DETAILED DESCRIPTION OF THE PREFERRED EMBODIMENTS

In accordance with the preferred embodiments of the invention, the particulate antiperspirant material comprises any compound having antiperspirant activity. Preferably, the antiperspirant materials used include astringent metallic salts, particularly including the inorganic and organic salts of aluminum, zirconium and mixtures thereof. Suitable antiperspirant aluminum or zirconium salts are any of those well known in the art, such as those discussed at length in U.S. Pat. Nos. 4,174,386, 4,806,338 and 4,840,786. The amount of antiperspirant active particulate material in the composition according to the invention may vary from about 25 to 100 wt. % of the total content of particulate materials.

The antiperspirant composition of the preferred embodiments of the invention further includes particulate filler material. Filler material is used to reduce the amount of propellant required in the final composition. In accordance with the invention, the preferred filler material is aluminum starch octenyl succinate, which is a modified corn starch commercially available under the trade name Dry Flo from National Starch and Chemical Corporation, Finderne Avenue, P.O. Box 6500, Bridgewater, N.J. 08807. The amount of filler material in the final composition may vary from 0 to about 75 wt. % of the total content of particulate material.

In accordance with the invention the combined amount of antiperspirant active and filler particulate materials lies in the range of 10 to 35 wt. %.

As is well known in the art of aerosol antiperspirant compositions, the particulate material is suspended in a hydrophobic emollient liquid carrier comprising one or more oils. The emollient liquid carrier improves initial adhesion of the suspended powders to the skin, thus aiding in the capture of the antiperspirant material by the skin as it is dispensed in spray form. Also, the carrier serves as a diluent, lubricant or spreading agent to facilitate uniform distribution of the antiperspirant material on the skin. Suitable emollient liquid carriers are disclosed in U.S. Pat. Nos. 4,822,596 and 4,904,463, the disclosures of which are specifically incorporated by reference herein. In accordance with the preferred embodiments of the present invention, the emollient liquid carrier is a mixture comprising cyclomethicone, isopropyl palmitate and dibutyl phthalate. In particular, the cyclomethicone used is the cyclic pentamer of dimethyl siloxane having a molecular weight of about 370. The amount of emollient liquid carrier in the composition according to the invention may vary from about 5 to about 50 wt. %.

In order to prevent caking or settling out of the astringent salt in the hydrophobic emollient liquid carrier, a bulking or suspending agent is incorporated in the composition of the invention. The suspending agent assists in filling the void space between suspended particles. The suspending agent is preferably a hydrophobically treated montmorillonite clays such as bentonites and hectorites. The hectorite and bentonite clays used in the invention have a layered clay structure which expands or swells on contact with water. One such commercially available clay is Bentone-38, which is a hectorite clay available from NL Industries, Inc. The amount of Bentone-38 in the composition of the invention may vary from about 0.2 to about 2.0 wt. %.

These clays are combined with an activator that enables the hectorite or bentonite clay to suspend the antiperspirant active particulate material in the hydrophobic liquid carrier. In accordance with the preferred embodiments of the invention, the activator is propylene carbonate. The amount of propylene carbonate in the composition of the invention may vary from about 0.01 to about 0.3 wt. %.

In accordance with the invention, the antiperspirant composition has no more than 60 wt. % of an aerosol propellant. The propellant gas according to the invention can be any liquefiable gas known to the art for use in aerosol containers. Examples of suitable propellants are trichlorofluoromethane, trichlorotrifluoromethane, trichlorotetrafluoromethane, monochlorodifluoromethane, difluoroethane, propane, butane or isobutane used singly or in combination. The amount of propellant in the composition of the invention should be no more than 60 wt. %.

In addition, the composition in accordance with the invention may incorporate allantoin and perfume. Allantoin is a known stimulator of cell proliferation and tissue growth. The addition of allantoin serves to reduce irritation caused to some sensitive individuals upon using any aluminum base product and even helps to heal such areas of irritation.

The method of manufacturing the antiperspirant composition in accordance with the invention comprises the following steps. First, the suspending agent, e.g., Bentone-38, and the propylene carbonate are dispersed in the isopropyl palmitate. The dispersion is stored for 15 to 20 min until it thickens due to swelling of the Bentone-38 in response to activation by the propylene carbonate. Then the oils, i.e., the cyclomethicone and dibutyl phthalate, are added to the dispersion. Thereafter, the solids, i.e., the antiperspirant and filler particulate materials, are added and the resulting dispersion is mixed. The mixture is homogenized using a Gifford-Wood shearing type homogenizer until it becomes a gel.

This gel constitutes the antiperspirant concentrate which is combined perfume and additional cyclomethicone inside the aerosol can. Then the can is pressurized by adding the aerosol propellant and sealed.

During experimentation performed by the inventors, regular 4-oz. cans having different valve and activator configurations were filled with the preferred antiperspirant aerosol compositions of the invention, that is, the modified corn starch formulations of Examples IV and VI (see below). After filling, the average spray rates were measured. The average spray rate for each type of can was based on the average measurement for three 10-sec sprays. The dimensional parameters for the different valve and activator configurations used in the experiments and the corresponding average spray rates are set forth in the following table:

| Config- uration | Stem Orifice* (inch) | Vapor Tap (inch) | Dip Tube Inner Diameter (inch) | Activator Orifice (inch) | Avg. Spray Rate (g/sec) |
| --- | --- | --- | --- | --- | --- |
| A | 1 × 0.018 | 0.025 | 0.042 | 0.019 | 0.56 |
| B | 2 × 0.018 | 0.031 | 0.050 | 0.020 | 0.67 |
| C | 2 × 0.018 | 0.030 | 0.050 | 0.020 | 0.60 |
| D | 2 × 0.018 | 0.025 | 0.050 | 0.020 | 0.84 |

*Number of holes times the dimension of the hole opening.

The average spray rates given above were obtained using the formulation of Example IV in cans with configurations A and D, and the formulation of Example VI in cans with configurations B and C.

The details of six examples of the antiperspirant aerosol compositions of invention, including the aforementioned Examples IV and VI incorporating chemically modified corn starch, formulated by the inventors are given in the following sections.

EXAMPLE I

An antiperspirant concentrate was prepared in accordance with the previously described procedure using the following formulation:

| Component | % (by weight) |
| --- | --- |
| Aluminum chlorhydrate (Reach 101) | 23.1812 |
| Talc (Cyprus Suprafino Talc) | 23.1812 |
| Bentone 38 | 2.2795 |
| Isopropyl palmitate | 24.6112 |
| Propylene carbonate | 0.6761 |
| Cyclomethicone (Pentamer) | 11.3559 |
| Dibutyl phthalate | 11.0686 |
| Allantoin | 3.6463 |

After the concentrate was homogenized, it had a viscosity of 124,800 cps measured on a Helipath Brookfield RVT viscometer using T-spindle "D" at 5 rpm.

The homogenized concentrate was then combined with A-46 hydrocarbon propellant, which is a mixture of 85% isobutane and 15% propane by weight of total propellant. The filling formula was as follows:

| Component | % (by weight) |
| --- | --- |
| Concentrate | 39.2 |
| Perfume | 0.3 |
| Cyclomethicone (Pentamer) | 0.5 |
| A-46 Propellant | 60.0 |

To fill a regular 4-oz. can required 48.75 gm of concentrate, 1.00 gm of perfume and 74.58 gm of A-46 propellant. Four cans were filled with the filling formula. Two cans had configuration A and two cans had configuration D. The talc formulation of Example I was sprayed from these cans without any problem.

EXAMPLE II

A second antiperspirant concentrate was prepared in accordance with the previously described procedure using the following formulation:

| Component | % (by weight) |
|---|---|
| Aluminum chlorhydrate (Reach 101) | 23.1812 |
| Corn starch | 23.1812 |
| Bentone 38 | 2.2795 |
| Isopropyl palmitate | 24.6112 |
| Propylene carbonate | 0.6761 |
| Cyclomethicone (Pentamer) | 11.3559 |
| Dibutyl phthalate | 11.0686 |
| Allantoin | 3.6463 |

The corn starch is commercially available from Argo.

After the concentrate was homogenized, it had a viscosity of 50,000 cps measured on a Helipath Brookfield RVT viscometer using the T-spindle "D" at 5 rpm. The homogenized concentrate was then combined with A-46 hydrocarbon propellant in accordance with the filling formula of Example I.

Four cans having the same hardware as the cans used for Example I were filled with the filling formula of Example II. The corn starch formulation of Example II was sprayed from these cans without any problem.

EXAMPLE III

Another antiperspirant concentrate was prepared as previously described using the following formulation:

| Component | % (by weight) |
|---|---|
| Aluminum chlorhydrate (Reach 101) | 23.1812 |
| Micronized polyethylene | 23.1812 |
| Bentone 38 | 2.2795 |
| Isopropyl palmitate | 24.6112 |
| Propylene carbonate | 0.6761 |
| Cyclomethicone (Pentamer) | 11.3559 |
| Dibutyl phthalate | 11.0686 |
| Allantoin | 3.6463 |

The micronized polyethylene-18 is commercially available from Allied Signal.

After the concentrate was homogenized, it had a viscosity of 57,200 cps measured on a Helipath Brookfield RVT viscometer using the T-spindle "D" at 5 rpm. The homogenized concentrate was then combined with A-46 hydrocarbon propellant in accordance with the filling formula of Example I.

Four cans having the same hardware as the cans used for Example I were filled with the filling formula of Example III. The polyethylene-18 formulation of Example III was sprayed from these cans without any problem.

EXAMPLE IV

Another antiperspirant concentrate was prepared in accordance with the previously described procedure using the following formulation:

| Component | % (by weight) |
|---|---|
| Aluminum chlorhydrate (Reach 101) | 23.1812 |
| Modified corn starch (Dry Flo) | 23.1812 |
| Bentone 38 | 2.2795 |
| Isopropyl palmitate | 24.6112 |
| Propylene carbonate | 0.6761 |
| Cyclomethicone (Pentamer) | 11.3559 |
| Dibutyl phthalate | 11.0686 |
| Allantoin | 3.6463 |

Dry Flo is a free-flowing, hydrophobically modified corn starch which has a soft, velvety texture and is insoluble in water at room temperature, i.e, has extreme resistance to wetting by water. Although Dry Flo is wetted by alcohol, propellants and organic solvents, it is insoluble in these materials. The screen analysis for Dry Flo is 99.5% of the particles pass through a 100-mesh screen.

Although Dry Flo is hydrophobic, it can adsorb moisture to an extent dependent upon the relative humidity of its surrounding environment. In aerosol systems, Dry Flo resists caking and agglomeration. It is compatible with and non-reactive toward perfumes and conventionally used emollients.

After the concentrate was homogenized, it had a viscosity of 50,000 cps measured on a Helipath Brookfield RVT viscometer using the T-spindle "D" at 5 rpm. The homogenized concentrate was then combined with A-46 hydrocarbon propellant in accordance with the filling formula of Example I. The Dry-Flo dispersed easily in the propellant and was easily delivered through standard powder valves without clogging.

Four cans having the same hardware as the cans used for Example I were filled with the filling formula of Example IV. In addition, two cans having configuration B and two cans having configuration C were filled. The modified corn starch formulation of Example IV was sprayed from these cans at good spray rates and without clogging.

The aerosol residue was analyzed to determine the level of aluminum chlorhydrate for some of the samples. The residue for the aerosols sprayed from the cans having configurations B and C had 33 and 29 wt. % aluminum chlorhydrate, respectively.

EXAMPLE V

Antiperspirant concentrate was prepared using the following formulation:

| Component | % (by weight) |
|---|---|
| Aluminum chlorhydrate (Reach 101) | 23.1812 |
| Sodium bicarbonate | 23.1812 |
| Bentone 38 | 2.2795 |
| Isopropyl palmitate | 24.6112 |
| Propylene carbonate | 0.6761 |
| Cyclomethicone (Pentamer) | 11.3559 |
| Dibutyl phthalate | 11.0686 |
| Allantoin | 3.6463 |

The sodium bicarbonate is preferably micronized.

After the concentrate was homogenized, it was combined with A-46 hydrocarbon propellant in accordance with the filling formula of Example I. The sodium bicarbonate formulation of Example III was sprayed from cans without any problem.

EXAMPLE VI

Another antiperspirant concentrate was prepared in accordance with the previously described procedure using the following formulation:

| Component | % (by weight) |
|---|---|
| Aluminum chlorhydrate (Reach 101) | 34.7718 |
| Chemically modified corn starch | 11.5906 |
| Bentone 38 | 2.2795 |
| Isopropyl palmitate | 24.6112 |
| Propylene carbonate | 0.6761 |
| Cyclomethicone (Pentamer) | 11.3559 |
| Dibutyl phthalate | 11.0686 |
| Allantoin | 3.6463 |

The modified corn starch was Dry-Flo, as in Example IV.

After the concentrate was homogenized, it had a viscosity of 28,600 cps measured on a Helipath Brookfield RVT viscometer using the T-spindle "D" at 10 rpm. The homogenized concentrate was then combined with A-46 hydrocarbon propellant in accordance with the filling formula of Example I.

Three cans having configuration B and three cans having configuration C were filled. The modified corn starch formulation of Example VI was sprayed from these cans at good spray rates with no clogging.

The preferred embodiments have been described in detail hereinabove for the purpose of illustration only. It will be apparent to a practitioner of ordinary skill in the art of aerosol antiperspirant formulations that various modifications could be made to the above-described formulas without departing from the spirit and scope of the invention as defined in the claims set forth hereinafter.

We claim:

1. An antiperspirant aerosol composition consisting essentially of:

10–35 wt. % of particulate material, 0.2 to 2 wt. % of a suspending agent to resist the tendency of the particulate material to settle out, 5 to 50 wt. % of liquid emollient carrier material for carrying the particulate material from the container to the skin in the form of a moist spray, and a propellant for expelling these components from a container, wherein said propellant makes up no more than 60 wt. % of said composition and said particulate material consists of either a particulate antiperspirant active material or a combination of said particulate antiperspirant active material and a particulate filler material selected from the group consisting of talc, sodium bicarbonate, corn starch, chemically modified corn starch, polyethylene, polyacrylate, and cross-linked polyurethane.

2. The antiperspirant aerosol composition as defined in claim 1, further consisting of allantoin and perfume.

3. The antiperspirant aerosol composition as defined in claim 1, wherein said suspending agent comprises hydrophobically treated hectorite clay and further comprising propylene carbonate for activating said hectorite clay.

4. The antiperspirant aerosol composition as defined in claim 1 wherein said particulate antiperspirant active material is selected from the group consisting of aluminum and zirconium antiperspirant salts and mixtures thereof and said propellant is selected from the group consisting of propane, butane, isobutane and mixtures thereof.

5. The antiperspirant aerosol composition as defined in claim 1 wherein said liquid emollient comprises isopropyl palmitate, cyclomethicone and dibutyl phthalate.

6. An antiperspirant aerosol composition consisting essentially of 10 to 35 weight percent of particulate material, 0.2 to 2 weight percent of a hydrophobically treated bentonite or hectorite clay or a mixture thereof as a suspending agent for said particulate material; 5 to 50 weight percent of a liquid emollient carrier material comprising isopropyl palmitate, cyclomethicone and dibutyl phthalate for carrying the particulate material to the skin in the form of a moist spray; 0.01 to 0.3 weight percent of propylene carbonate; a propellant selected from the group consisting of propane, butane, isobutane and mixtures thereof for expelling these components from a container wherein said propellant makes up no more than 60 weight percent of said composition and said particulate material consists of a particulate antiperspirant active material selected from the group consisting of aluminum and zirconium antiperspirant salts and mixtures thereof and a particulate hydrophobic chemically modified corn starch filler material; wherein more than 99% of the particles of said corn starch pass through a 100-mesh screen.

7. An antiperspirant aerosol composition as defined in claim 6 wherein said antiperspirant active material comprises aluminum chlorhydrate and said propellant is a mixture of propane and isobutane.

\* \* \* \* \* ns
REEXAMINATION CERTIFICATE (3739th)
United States Patent [19]

Ross et al.

[11] B1 5,605,682
[45] Certificate Issued Feb. 23, 1999

[54] ANTIPERSPIRANT AEROSOL COMPOSITION WITH HIGH SOLIDS CONTENT

[75] Inventors: Lloyd Ross, Hampton; Frank Schebece, Edison, both of N.J.

[73] Assignee: Colgate-Palmolive Company, Piscataway, N.J.

Reexamination Request:
No. 90/004,852, Dec. 3, 1997

Reexamination Certificate for:
Patent No.: 5,605,682
Issued: Feb. 25, 1997
Appl. No.: 238,195
Filed: May 4, 1994

Related U.S. Application Data

[63] Continuation of Ser. No. 869,996, Apr. 16, 1992, abandoned.
[51] Int. Cl.$^6$ .............. A61K 7/32; A61K 7/38; A61K 7/36
[52] U.S. Cl. ................... 424/68; 424/67; 424/47
[58] Field of Search ................... 424/68, 67, 47

[56] References Cited

U.S. PATENT DOCUMENTS 4,431,120  2/1984  Burger .................... 222/192

FOREIGN PATENT DOCUMENTS

| 1106329 | 8/1981 | Canada. |
| 1121730 | 4/1982 | Canada. |
| 028853 | 5/1981 | European Pat. Off.. |
| 1467676 | 3/1977 | United Kingdom. |

*Primary Examiner*—Alan L. Rotman

[57] ABSTRACT

An antiperspirant aerosol composition has a level of volatile organic compounds no greater than 60 wt. %. The composition includes particulate antiperspirant material and optionally particulate filler material. The filler material may be chemically modified corn starch, micronized polyethylene, cross-linked polyurethanes, polyacrylates, talc, sodium bicarbonate, corn starch, or any combination thereof. The antiperspirant aerosol compositions includes 10–35 wt. % of particulate material, 0.2–2 wt. % of a suspending agent, 5–50 wt. % of emollient carrier liquids and no more than 60 wt. % of an aerosol propellant mixture. The particulate material consists of 25 to 100 wt. % of a particulate antiperspirant active material and 0 to 75 wt. % of a particulate filler material. In addition, the antiperspirant aerosol compositions may contain certain optional components, such as activators, germicides, medicants, perfumes and colorants.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 6 and 7 is confirmed.

Claims 1–5 are cancelled.

* * * * *